United States Patent
Denise

(10) Patent No.: US 9,568,463 B2
(45) Date of Patent: Feb. 14, 2017

(54) OVULATION PREDICTION DEVICE

(71) Applicant: Hilin Life Products, Inc., Newark, NJ (US)

(72) Inventor: Helen Denise, Paramus, NJ (US)

(*) Notice: Subject to any disclaimer, the term of this patent is extended or adjusted under 35 U.S.C. 154(b) by 374 days.

(21) Appl. No.: 14/204,219

(22) Filed: Mar. 11, 2014

(65) Prior Publication Data

US 2014/0313322 A1    Oct. 23, 2014

Related U.S. Application Data

(60) Provisional application No. 61/781,440, filed on Mar. 14, 2013.

(51) Int. Cl.
*G01N 33/487* (2006.01)
*A61B 10/00* (2006.01)

(52) U.S. Cl.
CPC ......... *G01N 33/487* (2013.01); *A61B 10/0012* (2013.01); *A61B 2010/0019* (2013.01); *A61B 2010/0025* (2013.01)

(58) Field of Classification Search
CPC .... H04N 7/18; G01N 33/487; A61B 10/0012; A61B 10/0064; A61B 2010/0019; A61B 2010/0025
USPC ....................................... 348/135, 77, 79, 80
See application file for complete search history.

(56) References Cited

U.S. PATENT DOCUMENTS

| | | | | |
|---|---|---|---|---|
| 5,209,238 A * | 5/1993 | Sundhar | ............ | A61B 10/0012 600/551 |
| 5,914,271 A * | 6/1999 | Law | ............ | A61B 10/0012 436/164 |
| 6,451,619 B1 * | 9/2002 | Catt | ............ | A61B 10/0012 422/402 |
| 6,592,529 B2 * | 7/2003 | Marett | ............ | A61B 10/0064 600/551 |
| 6,793,886 B1 | 9/2004 | Weissmahr | | |
| 6,951,631 B1 * | 10/2005 | Catt | ............ | G01N 21/8483 422/404 |
| 7,369,331 B2 | 5/2008 | Sachdev et al. | | |
| 8,506,229 B2 | 8/2013 | Ogeron | | |
| 2003/0179446 A1 | 9/2003 | Yeh | | |
| 2006/0018043 A1 | 1/2006 | Gontier | | |
| 2011/0282247 A1 | 11/2011 | Denise | | |

* cited by examiner

*Primary Examiner* — Trang U Tran
(74) *Attorney, Agent, or Firm* — Chan Hubbard PLLC; Keala Chan

(57) ABSTRACT

This disclosure provides a stand alone electronic device to predict a likely time of ovulation based on crystal formation in a mucous body fluid sample. Optionally body temperature data may also be measured and saved on the device memory. The device allows user to save the data, download images, and compare results from different times. The disclosure further provides a device that includes software using an algorithm to calculate frequency of crystals on the sample and allowing comparison of the frequencies. The algorithm may use the temperature data also. The device includes an option to transfer data onto a smart phone or similar device. The device is suitable for predicting ovulation of any mammal, including human beings, dogs and livestock including horses.

24 Claims, 4 Drawing Sheets

A B C

OVULATION PREDICTION DEVICE

PRIORITY

This application claims priority of the U.S. Provisional Application No. 61/781,440 filed on March 14th 2013, the contents of which is incorporated herein by reference in its entirety.

FIELD OF THE INVENTION

The present invention relates to devices for prediction ovulation of mammals. The invention particularly relates to prediction of ovulation of human beings, dogs and livestock conforming approximately to the human ovulation model and exhibiting a non-seasonal pattern of ovulation at regular intervals.

BACKGROUND OF THE INVENTION

A woman can get pregnant only during a short period of time during the ovulation. Usually this is a window of about 12 to 24 hours during a monthly cycle. A healthy young couple has about a 20 percent chance of getting pregnant during a monthly cycle. In the modern society couples desire to have their first child in their late twenties or early thirties. It is not uncommon for couples to try to get pregnant in their late thirties or early forties either. As the probability of getting pregnant gets smaller with increasing age, it becomes necessary to predict the most likely time to get pregnant, i.e. the time of ovulation.

The commonly used methods for predicting ovulation include recording base body temperature and which some women find tedious and time taking. Specifically, as it may not be enough to measure the temperature just during one cycle, but the woman would need to follow the body temperature for several months to get an idea of the pattern of the cycle.

Accordingly there is need for a method to predict ovulation and to save the data to see the pattern of the cycle. Also there is a need to share the data of longer period of time with a doctor.

Similarly, there is a need for animal breeders to predict a likely time for the female animal to become pregnant. For example, horses are seasonal breeders, meaning that there are specific times during which they are able to reproduce. Typically they breed in the spring and the summer months. The menstrual cycle of an average mare is 21 days. Estrus lasts for 5 days to 1 week. Ovulation typically occurs one to two days before the end of estrus. Fertilization is possible for up to 30 hours after ovulation takes place. While feral and wild horses breed successfully without human assistance, planned mating is used to produce specifically desired characteristics in domesticated horses. For this purpose there is a need for a device to predict the likely time frame of a mare to become pregnant.

Similarly, there is a need for dog breeders to predict the likelihood of a bitch to become pregnant.

This invention utilizes a unique device to predict ovulation based on hormonal changes which occur in a female during ovulation and the resultant change in the make-up of her bodily fluids during this important time. This device utilizes the phenomenon known as "ferning" wherein a specimen of dried fluid sample produces crystals of a particular characteristic which is indicative of ovulation.

Georgios Papanicolaou described in 1945 how crystals were formed when a drop of cervical mucus was placed on a saline-free glass slide and allowed to air dry. Rydberg and Madsen (Rydbergm E. and Madsen V 1948. Acta Obst. And Gynec. Scandinay. 28:386) characterized the crystals to be common salt and the formation of the crystals was shown to be due to the prescience of mucine. Zondek and Rozin reported in 1954 (Zondek, B. and Rozin, S. 1954 Obst. and Gynec. 3: 463) that the crystallization is not specific for cervical mucus and that the same phenomenon appears in all mucus secretions and in most body fluids. The crystallization is called ferning, as the crystals have a fern-like pattern on the slide.

In presence of estrogen, just prior to ovulation, the cervical mucus, or other body fluid mucus forms fern-like patterns due to crystallization of sodium chloride on mucus fibers. This phenomenon is used to provide indirect evidence ovulation and fertility. However, this test does not predict the time of ovulation, but it gives indications of likely time of becoming pregnant.

There are several devices for ovulation prediction using detection of body fluid characteristics in the known art:

U.S. Pat. No. 6,793,886 is directed to a kit for the detection of characteristic and parameters of body fluids, such as saliva, urine and cervical mucus for identifying fertility comprising a set of flat plate-shaped supports for ampoules of said body fluids and a viewer provided with an enlargement means. Each of said flat plate-shape supports for body fluid present a shallow basin or trap with a convex bottom with a raised rim, and is equipped with locking fins for coupling with the viewer.

US 2003/0179446 is directed to a portable microscopic visualization tube for determining ovulation from saliva assay. It has a microscopic lens module, a beam tube, an electric powered LED mechanism, and a tube cap, and the LED mechanism includes a button battery seat, characterized in that the mounting position of the edge of the button seat and the inner wall of the beam tube is correspondingly formed in recessing block of protruding block such that the entire LED mechanism can be withdrawn from the beam tube to replace the battery.

US 2006/0018043 is directed to a portable handheld fertility/ovulation tester that uses ambient light. A sample holding frame and adjustable lens assembly is inserted into a light chamber in the bottom of the tester. An aperture in the bottom of the chamber is aligned with a microscope lens assembly and is sized to provide ambient light for the microscope lens assembly. The aperture may also have an optional light gathering lens to increase illumination. The adjustable lens assembly is threaded into a sample plate frame having a transparent sample plate. The microscope lens assembly is removably mounted onto the light chamber such that when the fertility ovulation tester must be held with the aperture pointed towards an ambient light source in order to observe the sample.

U.S. Pat. No. 7,369,331 provides a fixed focus ovulation tester comprising an inner casing, having a top and a bottom end; a controllable illuminating assembly located inside the inner casing and near the bottom end of the inner casing and being sealed at the bottom by a bottom face plate and a fixed focus eye piece assembly having a bottom inner portion for placing a biological specimen and a top outer portion for viewing the specimen being removably located at the top end of the inner casing.

In all of the above devices a spherical lens is used. In the case of a spherical lens, light enters the lens both along its axis and distant from the axis. This creates an aberration producing a blurry image around the perimeter of the image field. This is noticeable with the human eye, causing the user to attempt to refocus the image, and is more particularly noticeable when utilizing electronic imaging. Further, light entering these lenses anti-parallel to the axis produces a coma aberration and results in a hazy image, especially when viewing crystals spread across a finite surface.

An improvement to the lenses is provided in U.S. patent application Ser. No. 13/076,727 which discloses a hand held ovulation predictor device for women, which includes an ovulation predictor device body, an optical subassembly containing one or more aspheric lenses, an objective mount and a focus ring being movably connected to the ovulation predictor objective mount.

The entire prior art devices require that the user remembers how the samples looked earlier. There is no way to compare previous samples, nor is there a way to build any kind of liable record of the findings. None of the prior art devices allow the user to save any data or pictures, manipulate the data or share the information with her doctor.

There are various tests and devices to determine pregnancy of a mammal animal, other than a human being. However, there are no simple means to predict ovulation of the animal.

The invention according to this disclosure provides solutions to the flaws or currently available devices and practices.

SUMMARY OF THE INVENTION

It is an object of this invention to provide an electronic device to predict ovulation of a mammal from presence of crystal formation in a mucous body fluid sample, said device comprising: a housing having a display, user controls, a data transfer port, and a receptacle for a sample; an optics unit, a microprocessor unit, a light source, a heating/drying unit, an autofocus feature and a CCD array inside the housing; wherein the user controls control the microprocessor, the microprocessor controls the light source, the autofocus feature, the heating/drying unit, and the display, and wherein upon inserting a sample into the receptacle the CCD array captures an image focused with the autofocus feature, and wherein the image is converted to a digital format, saved on the memory and capable of being downloaded for viewing via the optics unit.

It is another object of this invention to provide a method to predict ovulation time of a mammal from presence of crystal formation on a mucous body fluid sample, said method comprising the steps of: a) providing a mucous body fluid sample on a glass plate and inserting the sample on the glass into a device, wherein the device comprises: a housing having a display, user controls and a receptacle with a heating unit for a sample; and an optics unit, a microprocessor unit, a light source, an autofocus feature, and a CCD array inside the housing; wherein the user controls control the microprocessor, the microprocessor controls the light source, the heating unit and display; b) allowing the heating unit dry the sample and CCD array capture an image and convert it to a digital format; c) saving the picture on the memory; and d) comparing frequency of crystals on the sample to frequency of crystals on previously taken figures, wherein increased number of crystals is indicative of ovulation.

It is a further object of this invention to provide a method to predict ovulation of a mammal from presence of crystal formation on a body fluid sample, said method comprising the steps of: a) providing a saliva sample upon waking in the morning before drinking, eating or smoking in a groove of a transparent slide; b) inserting the transparent slide into the receptacle of the device of claim 1; c) taking an image of the sample with device of claim 1; d) saving the image on the memory of the device of claim 1; e) measuring body temperature and saving temperature date on the memory of the device of claim 1; f) repeating steps a) to e) every morning upon waking at least for 30 days; and g) comparing frequency of crystals on the picture to a frequency of crystals on previously taken photographs, and comparing the body temperature to previously measured temperature; where the ovulation is predicted when the frequency of the crystals and the temperature reading are higher than previously.

It is an object of this invention to provide a device for predicting ovulation of a mammal, specifically ovulation of a human being, a horse or a dog.

It is a further object of this invention to provide a device predicting ovulation of a mammal by using a saliva sample.

It is another object of this invention to provide a stand-alone electronic device capturing the ferning pattern of the saliva of an ovulating female for prediction of most likely time to get pregnant.

It is yet another object of this invention to provide a standalone electronic device capturing the ferning pattern of a female for prediction of most likely time to get pregnant and allowing saving a large number of images and sharing the images with a doctor.

A further object of this invention is to provide a device imaging characteristics of a saliva sample and recording the images.

Yet another object of this invention is to provide a device recording images of saliva samples and using an algorithm to predict ovulation based on data from the recorded images.

Yet another object of this invention is to provide more accurate prediction of ovulation time based on combined information from data recorded from images of saliva samples and temperature readings from the female mammal during testing time.

It is an object of this invention to provide a device and a method to predict the likely time of a human female to become pregnant.

It is another object of this invention to provide a device and a method to predict the likely time of a mare to become pregnant.

It is yet another object of this invention to provide a device and a method to predict the likely time of a bitch to become pregnant.

It is a further object of this invention to provide a method for dogs and livestock breeders to determine the best timing for a planned mating.

For human use specifically, the device and method of this invention is useful for individuals desiring pregnancy but suffering from infertility. The device and method is useful for those who are first timers in trying to conceive. The device and method is preferred for those who want to rely on natural family planning. The device and method of this invention provide an inexpensive way to learn and track one's ovulation cycle. The device and method are also of useful for those who do not want to become pregnant but cannot or don't want to use other birth control methods but timing.

DESCRIPTION OF THE PREFERRED EMBODIMENTS

Figure 1:
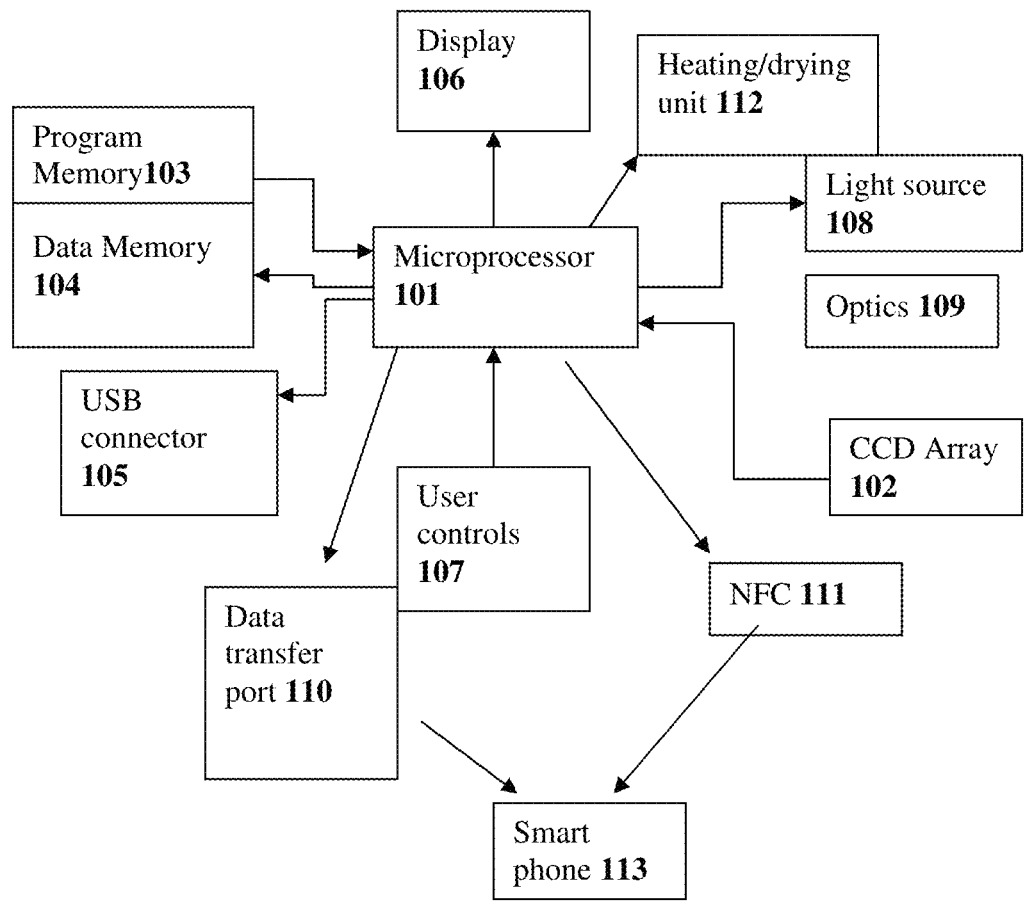
FIG. 1 is a block diagram of the components of the novel ovulation prediction device of the instant invention.

The preferred embodiments of the instant invention are now described referring to FIGS. 1, 2A, 2B and 3. Identical elements in the various figures are identified with the same reference numerals. Reference will now be made in detail to embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIG. 1, a block diagram of the invention is shown. A microprocessor 101, a charge coupled device (CCD) image capture array 102, Program Memory 103, Data Memory 104, USB connector 105, Display 106, User Controls 107, Light Source 108, Optics 109, Data Transfer Port 110, Near Field Communications (NFC) feature 111, heating/drying unit 112 and a smart phone 113 are shown.

Still referring to FIG. 1, according to a preferred embodiment the user turns the device on from User Controls 107. The microprocessor 101 having a program memory 103 and data memory 104 will turn the light source 108 on once a sample is inserted in the device. A preferred embodiment also has a heating/drying unit 112 at a sample receptacle to dry the saliva sample after inserting the sample on a transparent plate in the device. The microprocessor 101 turns the heating element of the heating/drying unit 112 on upon inserting the sample and off once the sample is dry. According to one preferred embodiment the device includes a thermosensitive element that turns on when the sample receptacle contacts the element upon inserting the sample into the device and turns off when the sample is dry. According to one preferred embodiment the microprocessor 101 turns the heating/drying unit off after a predetermined time period, for example 30 seconds after the sample is inserted into the sample receptacle.

The device has an autofocus features, focusing automatically to the saliva sample. Preferably the magnification is 100×, but any magnification showing the ferning pattern can be used. The user can then take an image of the desired view of the sample by using user controls 107 to activate the CCD 102 to capture the image and convert it on digital values. Data may then be saved on an internal or external memory, such as a memory stick. The memory preferably has capacity to at least 365 images. i.e. one image each day of the year.

According to one preferred embodiment, the user may select one or more of the saved images for viewing and comparing them on the display 106. According to one preferred embodiment the display can display at least two images simultaneously. According to one preferred embodiment there are template images saved in the device memory and the display is capable of showing simultaneously one or more template images and one or more images of user's saved data.

According to a preferred embodiment the images may be transferred and saved on a smart phone 113 or a tabloid. The user may then share the pictures for example with her doctor via email or text messages and can easily bring the pictures to her next appointment. According to one preferred embodiment the device has a NFC-feature 111 and the date can be transferred wirelessly.

According to a preferred embodiment the user takes a picture of her saliva sample every morning when she wakes up before eating, drinking or smoking. It is not necessary to take any more than one image per day. The most reliable results of ovulation likelihood are received by taking the image at the time of waking up before eating, drinking or smoking. The user can then share the saved data with her doctor.

According to one embodiment the device includes software capable of using an algorithm to provide a sampling schedule for the user to provide samples. According to this embodiment the device provides a schedule for sampling around the most probable time of the ovulation. The device may provide an alarm or notification for the user for sampling. The alarm or notification may be a voice, light, or shaking of the device.

According to a preferred embodiment the device has heating/drying unit 112 controlled by the microprocessor. The heating element of the unit 112 dries the sample within few seconds whereby the sample can be inspected, displayed and saved immediately. According to one preferred embodiment the user may provide a pre-dried sample. Such pre-dried sample may for example be air dried sample.

According to a preferred embodiment the user control includes means to insert the date of the sample. Via the optics unit the user may view images saved in the memory and choose any desired date, e.g. the first day of each month to be viewed or images of every day of a desired month.

Figure 2A:
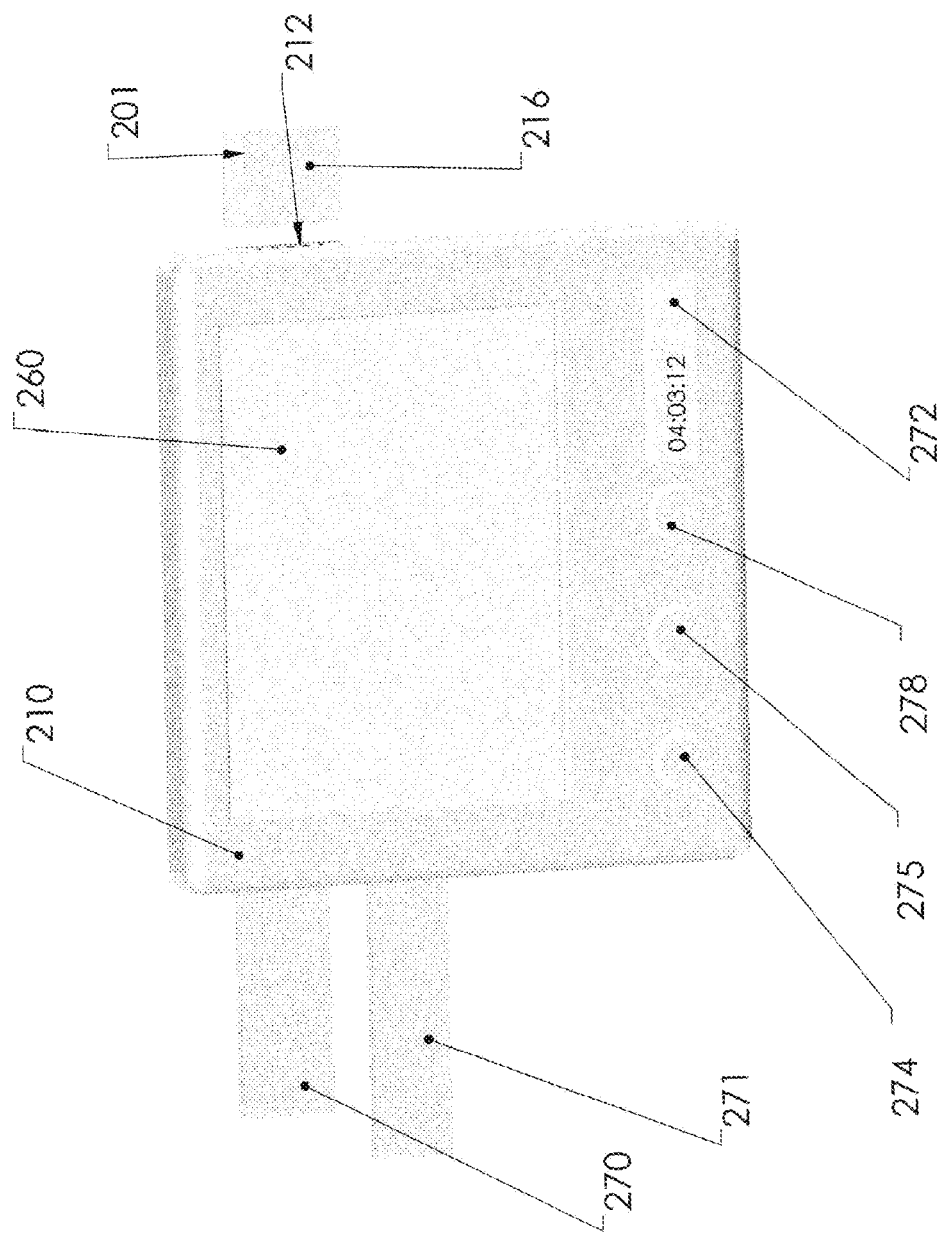
FIG. 2A. is a front perspective view of the novel ovulation prediction device of the instant invention.

Now referring to FIG. 2A, the device is shown in a front perspective view. The figure shows a housing 210, a display 260, user controls defined as a date control 272, on/off button 274, take a picture button 275 and search button 278, a receptacle 212 to insert a sample, a transparent slide 216 with an orientation groove 201 to consistently place the sample on, and memory stick(s) or other memory device 270, 271 to save the data. The memory device may for example be a smart phone (111 in FIG. 1).

Still referring to FIG. 2A, the user places a sample on the transparent slide 216. The transparent slide may be a glass slide. The sample is most preferably a drop of saliva, but it can as well be a drop of cervical fluid. The transparent slide 216 having the sample is now pushed into the sample receptacle 212 (which has a relief 202 (shown in FIG. 2B) to protect the sample) of the device. The device is turned on using the on/off-button 274. In a preferred embodiment turning the device on will turn on the heating/drying unit (112 in FIG. 1) to dry the sample on the transparent plate (e.g. glass) within second(s). Turning the device on will also turn the light source (not shown in FIG. 2A) on. The light source is preferably a LED light and it illuminates the sample. The device has an autofocus feature and the image of the sample (see FIGS. 3A-C) is displayed on the display screen always in focus. The user has to set the date from the date control 272. Through the take-a-picture button 275 the user is activating the CCD (102 in FIG. 1) to capture the picture and transform it into digital format. The microprocessor saves the pictures with the date information. The user may download the images taken on different days through the optics unit (109 in FIG. 1), print the saved images, or transfer them to another suitable device, e.g. a smart phone to email the images for example to her doctor.

The device is preferably handheld and can be run with batteries. The device may also be charged (receptacle in FIG. 2B).

Figure 2B:
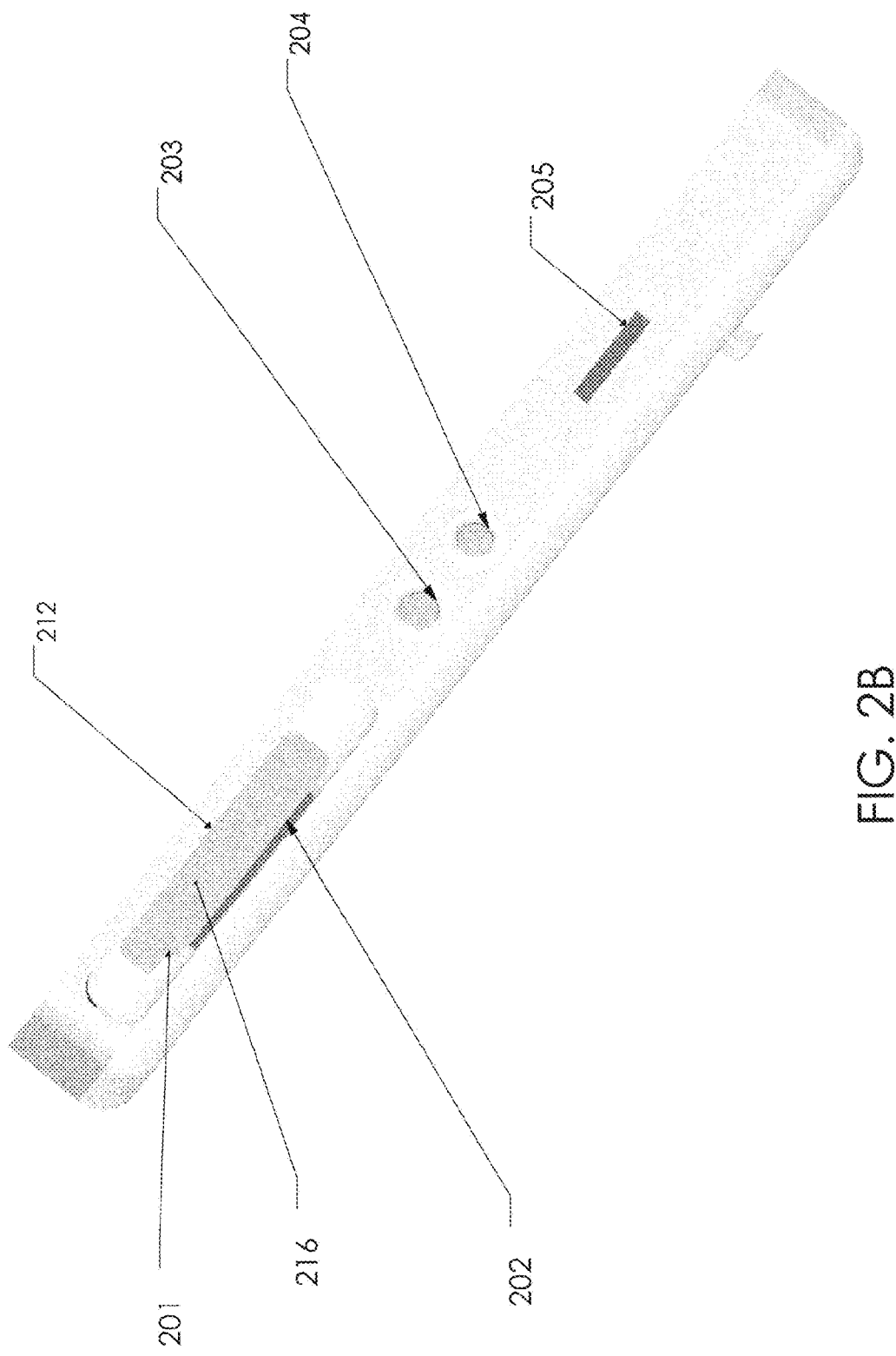
FIG. 2B is a side perspective expanded view of the novel ovulation prediction device of the instant invention shown in FIG. 2A.
Figure 3:
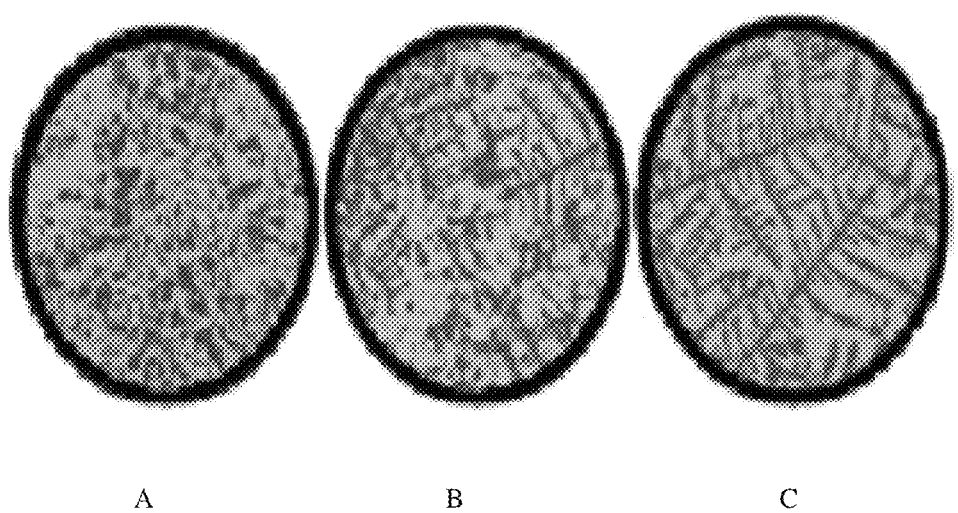
FIG. 3 A, B, C show images of saliva of a female as captured with a novel ovulation prediction device of the instant invention. Image A shows a saliva sample of a non ovulating female. Image B shows a saliva sample with few ferning patterned crystals indicating that the ovulation is approaching or just passed. Image C shows a saliva sample on the ovulation date.

Now referring to FIG. 2B, the device is shown in a side perspective expanded view. The figure shows a transparent slide 216 with recess or a groove 201 for consistency of orientation of the samples, a receptacle 212 (see FIG. 2A and FIG. 2B) to inset a sample and a relief 202 to prevent damaging of the samples. The figure shows receptacles 203, 204 are temperature information to the user. This embodiment allows the user to record her body temperature and save the data into the memory of the device. According to a preferred embodiment the user measures her temperature with a thermometer(s) attached to inlet 203 or 204 in the morning. The user can save the data on the device memory with the date and time information. The user then provides a saliva sample and takes pictures as described above. This data can be saved along with the temperature data. In FIG. 2B 205 is receptacle for battery charging.

The stored images and the temperature data and associated algorithmic data (see below) may be transferred through a number of generally accepted methodologies including a smart phone (113 in FIG. 1). A direct data transfer may occur through a data transfer port (110 in FIG. 1). In such a scenario, the data transfer port receives a cable which enables the user to transfer selected data to a secondary device much like the transference of images and data from a digital camera to a computer. Alternatively, the data transfer port may accept a secure digital (SD) card that enables an arbitrary amount of storage depending on the card selected. The SD card can then be readily transferred to a secondary device and the data saved to that card can then be uploaded to the secondary device. Even yet, in embodiments where no such data transfer port exists, the device may use near field communications (NFC) (111 in FIG. 1) to transfer data between devices. This method enables the wireless transfer of data via radio wave communication.

In a preferred embodiment the user may manipulate the saved data in a way that the results may be compared to pre-determined norms derived from many other user samples or to template data saved in the memory of the device. Furthermore, the microprocessor may be programmed to use one or more algorithms to provide prediction of likely ovulation time and to provide a sampling schedule for the user. Generally, the ferning pattern (see FIG. 3) in the saliva sample is created by the crystallization of sodium chloride in the presence of increased hormone levels such as estrogen. Estrogen and the associated estrogen levels are key factors is determining potential fertility. The increase in estrogen, in turn, results in an increase in the crystallization pattern, which is detected by the CCD and stored in the computer readable memory within the device. The microprocessor analyzes the stored images for detecting crystallization lines via optical analysis within a given sample based on the known parameters (i.e. size, resolution, etc.) of the image captured by the CCD. The microprocessor can then arrive at a value for the degree of crystallization of a given sample to make a determination whether the level of crystallization meets or exceeds an accepted or arbitrary level determined to signify peak ovulation. Thus, this numerical figure can then be compared either manually by the tester or automatically by the device to signify whether or not the tester has reached peak ovulation.

According to another embodiment the device may also include a unit to measure body base temperature or other parameters and the software may use an algorithm to utilize that data in addition to the data captured from the body fluid sample.

According to a preferred embodiment the device is handheld. The measures of the housing may be about 2.5" times 3" times 0.5" (6.35×7.62×1.27 cm). A hand held device is preferable when the device is meant for predicting ovulation of human females. The device may be more robust in its size when it is meant to be used for dogs and livestock breeders.

It is understood by a skilled artisan that several changes and alterations may be made to the device and method without diverting from the spirit of this invention.

What is claimed is:

1. An electronic device to predict ovulation of a mammal from presence of crystal formation in a mucous body fluid sample, said device comprising:
   a housing having a display, user controls, a data transfer port, and a receptacle for a sample;
   an optics unit, a microprocessor unit, a light source, a heating/drying unit, an autofocus feature and a CCD array inside the housing;
   wherein the user controls control the microprocessor, the microprocessor controls the light source, the autofocus feature, the heating/drying unit, and the display, and wherein upon inserting a sample into the receptacle the CCD array captures an image focused with the autofocus feature, and
   wherein the image is converted to a digital format, saved on the memory and capable of being downloaded for viewing via the optics unit.

2. The device of claim 1, wherein the sample is a fresh or a pre-dried saliva sample.

3. The device of claim 1, wherein the sample is inserted into the receptacle on a transparent slide, said slide having a groove for the sample.

4. The device of claim 1, wherein the heating/drying unit has a thermo sensitive element that upon inserting the sample slide into the receptacle becomes in contact with the slide and turns on, and turns off upon the sample being dried, or after a predetermined time.

5. The device of claim 1, wherein the user controls comprise on/off-button; search-button; date control; and take a picture-button.

6. The device of claim 1, wherein the device can be coupled with a smart phone or a tablet, and the digital images may be saved in the smart phone or the tablet.

7. The device of claim 1, wherein the device includes software capable of using an algorithm to calculate a predicted ovulation time based on information retrieved from previously saved data.

8. The device of claim 1, wherein the device includes software capable of using an algorithm to calculate a predicted ovulation time based on comparative analysis between present test and template data.

9. The device of claim 5, wherein the device additionally saves body temperature data and the software is capable of using an algorithm to calculate a predicted ovulation time based on combined information retrieved from previously saved image and temperature data.

10. The device of claim 1, wherein the device includes software capable of using an algorithm to provide a sampling schedule for the user to provide samples.

11. The device of claim 1, wherein the device is battery operated.

12. The device of claim 1, wherein the memory has a capacity to save at least 365 images.

13. The device of claim 12, wherein the user can select one or more images and display them simultaneously to make comparisons.

14. The device of claim 13, wherein at least one of the images is a template image.

15. The device of claim 1, wherein the mammal is a human being, a horse or a dog.

16. The device of claim 1, wherein the data transfer port receives a removable storage device or data transfer linkage.

17. A method to predict ovulation time of a mammal from presence of crystal formation on a mucous body fluid sample, said method comprising the steps of:
   a) providing a mucous body fluid sample on a glass plate and inserting the sample on the glass into a device, wherein the device comprises: a housing having a display, user controls and a receptacle with a heating/drying unit for a sample; and an optics unit, a microprocessor unit, a light source, an autofocus feature, and a CCD array inside the housing; wherein the user controls control the microprocessor, the microprocessor controls the light source, the heating/drying unit and display;
   b) allowing the heating unit dry the sample and CCD array capture an image and convert it to a digital format;
   c) saving the picture on the memory; and
   d) comparing frequency of crystals formation on the sample to frequency of crystals formation on previously taken figures, wherein changed formation and increased number of crystals is indicative of ovulation.

18. The method of claim 17, wherein the mucous body fluid sample is a saliva sample.

19. The method of claim 17, wherein the device is coupled to a smart phone or a tabloid and the images are saved on the smart phone or the tabloid.

20. The method of claim 17 wherein the saved images are shared electronically with doctor and step d) is conducted by the doctor.

21. The method of claim 17, wherein in step e) the microprocessor uses a software and at least one algorithm to compare frequency of the picture of step d) to previously taken pictures, and wherein the microprocessor provides a prediction of the ovulation time.

22. A method to predict ovulation of a mammal from presence of crystal formation on a body fluid sample, said method comprising the steps of:
   a) providing a saliva sample upon waking in the morning before drinking, eating or smoking in a groove of a transparent slide;
   b) inserting the transparent slide into the receptacle of the device of claim 1;
   c) taking an image of the sample with device of claim 1;
   d) saving the image on the memory of the device of claim 1;
   e) measuring body temperature and saving temperature date on the memory of the device of claim 1;
   f) repeating steps a) to e) every morning upon waking at least for 30 days; and
   g) comparing frequency of crystals on the picture to a frequency of crystals on previously taken photographs, and comparing the body temperature to previously measured temperature; where the ovulation is predicted when the frequency of the crystals and the temperature reading are higher than previously.

23. The method of claim 22, wherein the saved images and temperature data are shared electronically with a doctor and the doctor conducts the step f).

24. The method of claim 22, wherein in step g) the microprocessor uses a software and at least one algorithm to compare frequency of the crystals of step g) to frequency in previously taken images, and temperature of step g) to previously saved temperature data, and wherein the microprocessor provides a prediction of the ovulation time.

* * * * *